United States Patent [19]
Poley

[11] Patent Number: 5,222,960
[45] Date of Patent: Jun. 29, 1993

[54] CRACKING AND ROTATING CATARACT FOR REMOVAL FROM EYE

[76] Inventor: Brooks J. Poley, 2 Greenway Gables, Minneapolis, Minn. 55403

[21] Appl. No.: 878,911

[22] Filed: May 5, 1992

Related U.S. Application Data

[62] Division of Ser. No. 592,994, Oct. 5, 1990.

[51] Int. Cl.⁵ .............. A61B 17/00; A61B 19/00
[52] U.S. Cl. ..................... 606/107; 606/1; 128/898; 623/4; 623/6
[58] Field of Search ............ 606/1, 107, 161, 166; 128/20, 898; 623/4, 6

[56] References Cited

U.S. PATENT DOCUMENTS

| | | | |
|---|---|---|---|
| 2,644,455 | 7/1953 | Benoit | 606/205 |
| 3,022,787 | 2/1962 | Daniel | 606/207 |
| 3,589,363 | 6/1971 | Banko | 604/22 |
| 3,882,872 | 5/1975 | Douvas et al. | 606/107 |
| 3,996,935 | 12/1976 | Banko | 606/107 |
| 4,257,406 | 3/1981 | Schenk | 606/107 |
| 4,597,388 | 7/1986 | Koziol et al. | 606/107 |
| 4,693,245 | 9/1987 | Pao | 606/107 |
| 4,825,865 | 5/1989 | Zelman | 606/107 |
| 4,957,505 | 9/1990 | McDonald | 606/107 |

FOREIGN PATENT DOCUMENTS

| | | | |
|---|---|---|---|
| 1457925 | 2/1989 | U.S.S.R. | 606/107 |
| 8906522 | 7/1989 | World Int. Prop. O. | 606/107 |
| 9002536 | 3/1990 | World Int. Prop. O. | |

OTHER PUBLICATIONS

Ocular Surgery News, May 15, 1990-p. 54-"No Fault insurance Don't try the nuclear splitting techniques without it".
Ocular Surgery News, Feb. 1, 1990-p. 32-Surgical Maneuvers— "Refinements to the hydrodelineation technique".
Ocular Surgery News, Feb. 1, 1990-p. 33-"Focus on Phaco—'Advanced phaco': time to consolidate".
Catalog-Grieshaber & Co. AG, Switzerland, Ophthalmic Surgical Instruments.
Ocular Surgery News, Apr. 1, 1990 (pp. 60, 61) "Focus on Phaco—Kinder, gentler, bite-sized approach".

Primary Examiner—Stephen C. Pellegrino
Assistant Examiner—Glenn K. Dawson
Attorney, Agent, or Firm—Wood, Herron & Evans

[57] ABSTRACT

A method and instruments for cracking a cataract nucleus into smaller segments and repositioning them within the lens capsule for removal from the eye by phakoemulsification. After a trough has first been formed in the nucleus, a "cracker" instrument having two separable blades is inserted into the trough and the blades are moved apart so that they press outwardly against the opposite sides of the trough and thereby split the nucleus in half. A "rotator" instrument having an enlarged angulated foot at the end of a narrow shank may be used to rotate the split segments in the capsule to position them for phakoemulsification. The cracking and rotating technique is easier and safer than the prior technique.

10 Claims, 4 Drawing Sheets

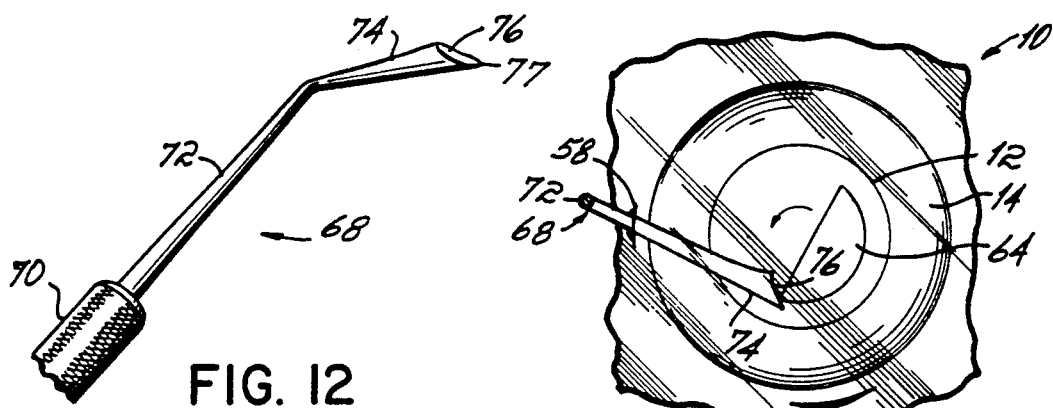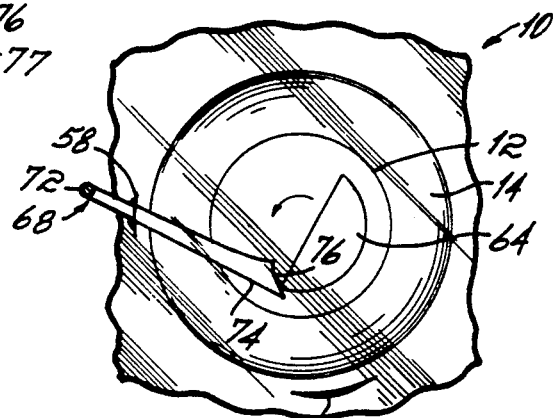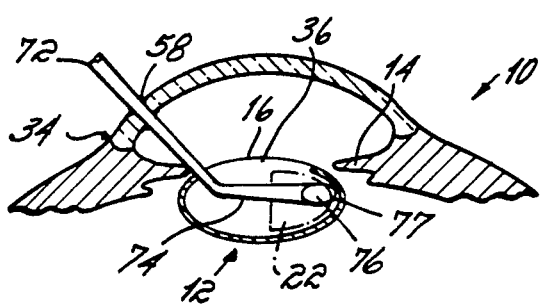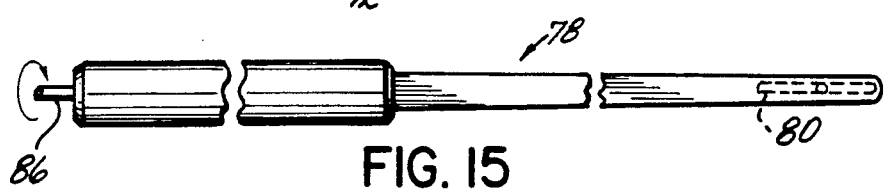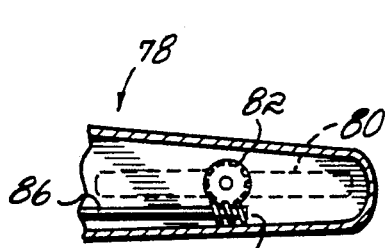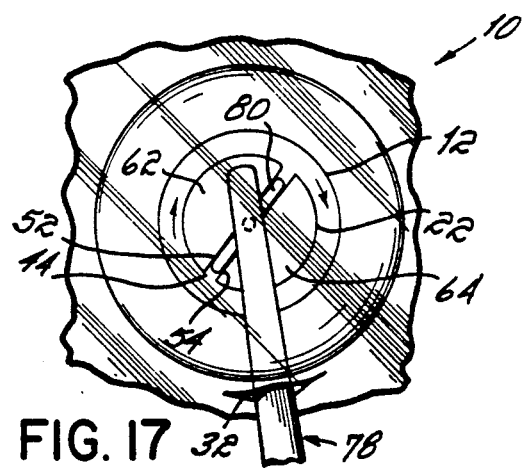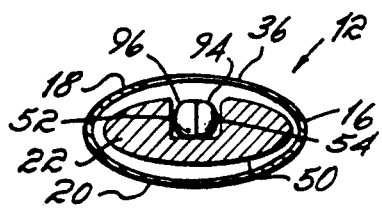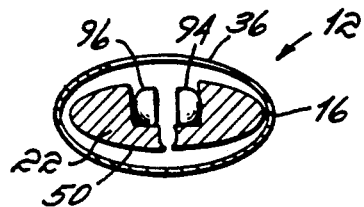

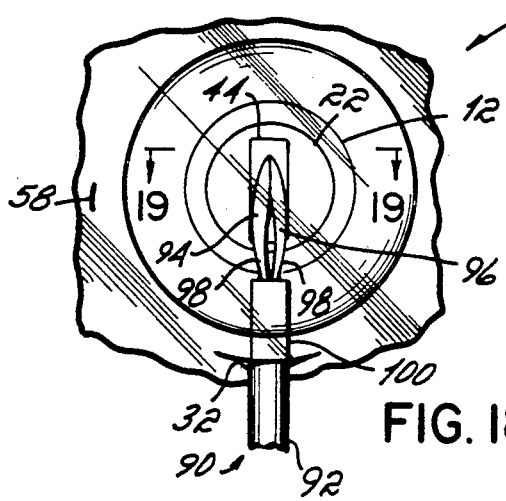
FIG. 18
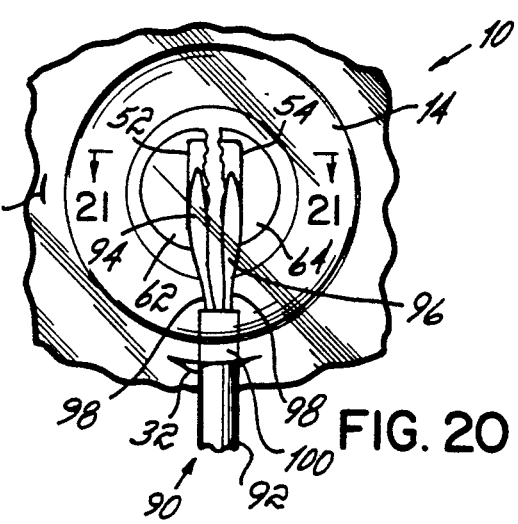
FIG. 20
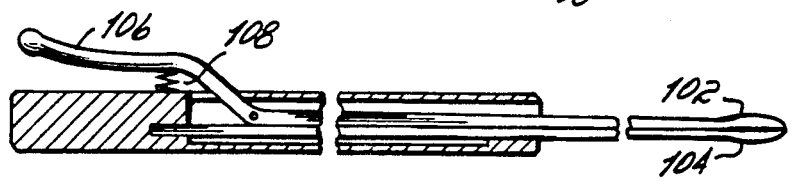
FIG. 22
FIG. 23
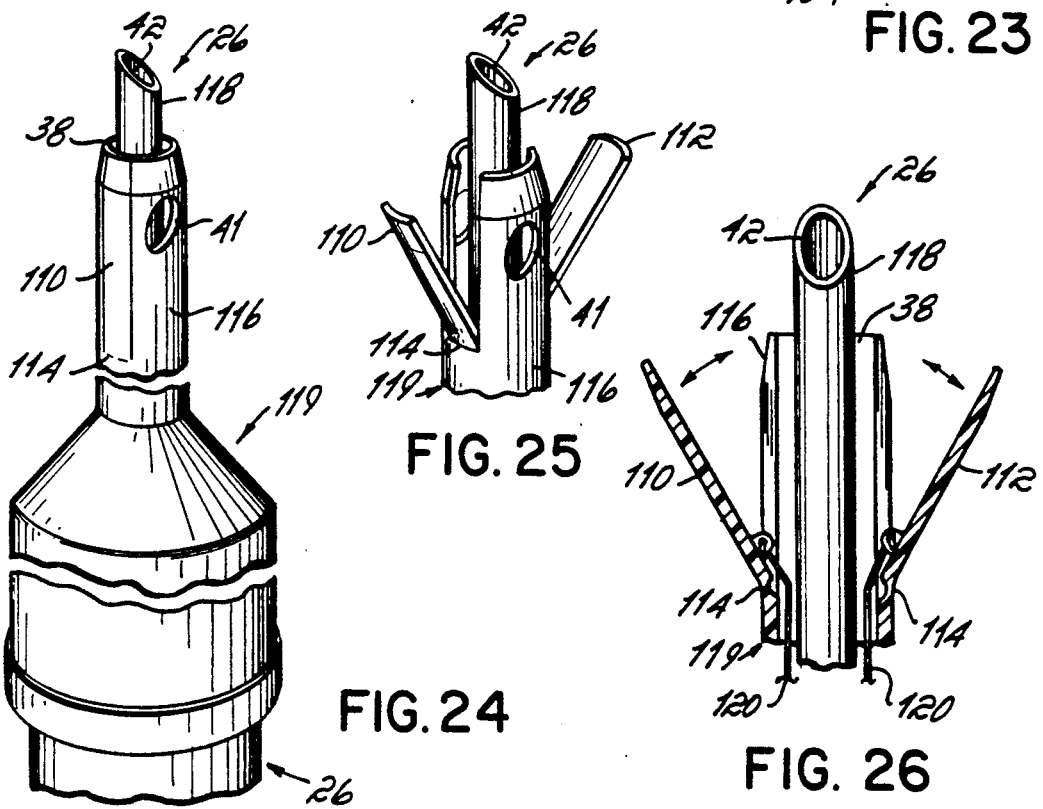
FIG. 24
FIG. 25
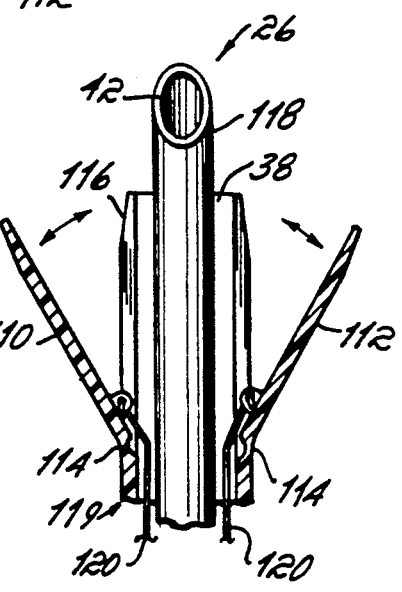
FIG. 26

CRACKING AND ROTATING CATARACT FOR REMOVAL FROM EYE

This is a division of application Ser. No. 592,994, filed Oct. 5, 1990.

FIELD OF THE INVENTION

This invention relates to the field of ophthalmology and more particularly to the removal of a cataract nucleus within the lens capsule of the eye.

BACKGROUND

When a cataract forms in the human eye, the nucleus of the lens becomes relatively hard and "crystalline," diffusing or scattering light passing through it, and partially or wholly loses its ability to focus. In order to remove the nucleus prior to implanting an artificial lens, the nucleus must be separated from the softer cortex around it inside the lens capsule, and then removed through an opening formed in the capsule.

In the well known phakoemulsification technique, which is becoming the procedure of choice for removing a cataract nucleus, the nucleus is pulverized or abraded by vibration of a "phako" tool. The phako tool has a tip or "needle" (about 3 mm in diameter) which is inserted through an opening in the capsule, into close proximity to the nucleus. High frequency reciprocation of the tip erodes the nucleus into tiny fragments which are then removed by aspiration (flushing) through the lumen or tube of the tip of the phako tool and removed from the eye. Saline is introduced into the eye between the tip and a sleeve around it. The saline fills the anterior chamber of the eye during the operation to facilitate movement of the cataract particles as they are broken up, aspirated into the needle lumen and flushed out of the eye. One potential danger of the phako technique is that it can very rapidly perforate the posterior lens capsule (which is obscured behind the cataract) if the tip contacts it.

THE PRIOR ART

In order to keep the phako tip at a safe distance from the posterior capsule and from the peripheral edge of the capsule, it is known to subdivide the nucleus into smaller "bite size" pieces which are phakoemulsified individually near the center of the capsule. In that so-called "fractional phako" system, the nucleus is grooved across its anterior face and split into quarter segments for easier removal.

More particularly, in the prior art fractional phako technique the nucleus is first separated from the cortex. This can be done, for example, by the "hydrodelineation" technique in which saline is injected to part the nucleus from the cortex along their interface. The nucleus is then troughed or grooved with the tip of the phako emulsifier. The tip is inserted through a primary incision, usually about 3 mm. wide, at the bottom or "12:00" position, and the trough is made vertically upward from that position. (Angular positions on the eye are referred to herein as viewed through the operating microscope, with 12:00 at the bottom of the eye; 9:00 at the left; 6:00 at the top, and so on, in accordance with conventional practice. "Vertical" means the direction between 12:00 and 6:00). The trough is made across only the central part of the nucleus; the iris lies between the phako tip and the near edge of the nucleus and thus blocks the tip; and the trough is stopped short of the far (6:00) edge so as not to injure the peripheral wall of the capsule which is obscured under the iris. Similarly, the trough is formed to a depth of only about ¾ of the thickness of the nucleus, so as to provide clearance from the obscured posterior capsule wall. Since the trough thus does not extend entirely across or through the nucleus, the phako tip remains spaced safely away from the capsule wall by the uncut nucleus and the surrounding lens cortex. The trough made by moving the phako tip along a linear path is surprisingly straight sided.

The half segments on each side of the trough are then separated by pushing them apart so as to "crack" or "split" the nucleus along the bottom of the trough. In the past this has been done by pressing the phako tip against one wall of the trough while simultaneously pressing a separate, blunt tool or probe against the opposite wall of the trough, until the nucleus separates along the "fault line" provided by the trough. The probe is inserted through a secondary incision at 9:00 position. The physician must use both hands to manipulate the two instruments in the two opposite directions; moreover, a soft nucleus may not split cleanly in that technique.

The lens segment halves so formed are still undesirably large, and it is known to quarter them for easier phakoemulsification. For that purpose the two halves, still within the capsule, are rotated 90° so that a second trough can again be made in the vertical direction, at right angles to the first. In the past this has been done by nudging the split segments around, using the phako tip as the pusher. The lower corner of the left half segment is pushed clockwise by the phako tip; the top of the left half abuts and pushes the right half. When the two halves have been turned 90°, the upper segment half is then troughed with the phako tip, and is split by pushing oppositely on the sides of its trough wall, again with the phako tip and a blunt probe inserted through the secondary incision. The two segment quarters so formed are then emulsified and removed. The remaining half, at the "bottom" of the capsule (i.e., the near side, below a 9:00-3:00 line) must then be rotated 180° to the top (far side) for troughing and splitting (it cannot be troughed on the near side because its peripheral edge is partly covered by the iris and the peripheral anterior capsular rim, over which the phako tip extends). This half is again rotated by pushing it around with the phako tip, so that it is then at the top of the capsule, opposite the primary incision. It is troughed, split with the assistance of a second probe, emulsified and removed. Further description of the prior art fractional phako technique is given in a series of articles in *Optical Surqery News*, issues of Feb. 1, 1990, pages 32 and 33; and Apr. 1, 1990, pages 60 and 61.

The two-tool prior art procedure for cracking the nucleus after it has been troughed, is relatively awkward and inconvenient. The physician must use two hands to insert and manipulate the two instruments to push the opposite sides of the trough apart from one another. Moreover, the procedure of rotating the segments, once split apart, with the phako tip is also relatively inconvenient and awkward. Thus there has been a need for a better method and means for splitting the nucleus into halves and quarters along the troughs and for rotating the split segments within the capsule.

BRIEF DESCRIPTION OF THE INVENTION

In accordance with the method of this invention, the troughed nucleus is split by a single "cracker" instrument, inserted through the primary incision. The cracker has two generally parallel wings or blades which fit in the trough and which are moved apart to press outwardly against the opposite sides or walls of the trough to crack the nucleus. The cracker is rather like a forceps, but the blades push apart rather than pinch. The trough can be relatively narrow, and should be no wider than needed to accommodate the cracker blades. The blades are preferably mounted around the phako tip itself and in closed position serve as a sleeve-like conduit for introducing saline solution into the capsule, thereby enabling the same tool to be used for troughing, cracking, and phakoemulsification, although a separate cracker instrument is also contemplated. The two blades are preferably semicircular in section and face one another (convex sides out), and are operated by means for selectively opening and closing them. Preferably the blades are hinged to the phako tool body on opposite sides of the base of the phako tip. They close to form a sleeve for insertion into the trough and are moved apart or opened after the trough has been formed, by operating a cam or link which swings them around their hinge points so that the blades diverge from the phako tip and engage the sides of the trough. The blades are preferably cammed at their base by a member which is movable rotationally or longitudinally in relation with them; alternatively a lever handle or a solenoid may operate the blades. With the cracker, even if it is separate from the phako tool, it is unnecessary to simultaneously manipulate two tools, as was previously required in the splitting step.

After the nucleus has been cracked in half, the halves are rotated 90° so that the upper half can be troughed vertically. Instead of using just the phako tip for this purpose as in the prior art technique, the rotation is carried out with the assistance of a second instrument comprising a special rotator tool, and the phako tip. The rotator tool is inserted through a secondary incision at the 9:00 position, which only need be about 1 mm. wide. The rotator has a narrow shank and an enlarged foot which provides a relatively large area for engaging and pushing on one lens half segment. The foot preferably has a concave face which is angled or cocked with respect to the shank. As the segment is rotated, the angle changes between the rotator face and the split line upon which it bears: as the segment moves it becomes gradually parallel to the rotator face. The face is shaped so that it will maintain good engagement with the segment as the segment is rotated. Maximum contact during rotation is maintained by providing an approximately 30° angulation of the face. Together, the angulation and relatively large surface area of the face provide a better "grip," especially on a soft nucleus. The rotator is preferably used to push clockwise on the upper corner of the right segment half, while the phako tip pushes clockwise on the lower corner of the left segment half. This "double push" facilitates rotation.

After the two cataract segment halves have been rotated about 90°, the rotator is removed and a vertical trough is formed in the upper segment, from the horizontal base of the segment toward but not to its far (top) edge. The cracker (either on the phako tip, or as a separate tool) is then inserted in the trough and opened to split the upper segment half. The two segment quarters are lifted and nudged toward the phako tip in the approximate center of the capsule using the rotator face as a spoon for this step. The quarters are removed while maintaining a safe distance between the tip and the capsule wall. A right handed physician may find it convenient to remove the right upper segment first, then the left.

After the two segment quarters have been removed from the far side of the capsule, only the lower half segment remains, which is in the near side of the capsule. It is then rotated 180° to place it at the top of the capsule, opposite from the primary incision, for optimum accessibility for troughing. A second rotator tool, which can be a mirror image of the first rotator tool, is preferably used for this second rotating step. To carry out this rotation the rotator is inserted from the 9:00 position, slipped under the capsule rim, and is engaged with the left side of the bottom segment half to turn it counterclockwise. This rotation is easier than the first because only the one half segment remains; it can readily be carried out with the rotator alone, without using the phako tip.

The bottom segment is rotated 180° with the rotator, to the top, and again the angulation of the face maintains better engagement with the segment than the phako tip would, as the angle between face and segment changes during the rotation. Once positioned at the top, this half is troughed, cracked with the cracker, emulsified and removed.

The invention also contemplates an alternative rotator device which is especially useful if the nucleus is unusually soft and adherent to the cortex. Under those circumstances the rotators described above may tend to pierce or cut through the soft nucleus material, rather than pushing it in a circular manner. In this alternative form, the rotator is in the form of a bar which is pivotally mounted below the end of a shaft. The rotator bar is inserted in the trough of the nucleus, preferably after it has been split, and is rotated relative to the shaft. As it turns it bears on the sides of the trough over relatively large areas, and turns the nucleus segment halves. When the rotation has been completed, the segments are depressed into the posterior chamber so that the bar can be lifted from the trough, turned to starting position, and withdrawn.

DESCRIPTION OF THE DRAWINGS

FIG. 3 is a plan view showing the nucleus being "troughed" by a phako tool;

FIG. 4 shows the troughed nucleus being split;

FIG. 5 is a cross sectional view taken on line 5—5 of FIG. 4;

FIG. 6 is a plan view showing the split segment halves being rotated;

FIG. 7 shows the split segment halves having been rotated 90°, preparatory to quartering;

FIG. 8 shows the troughing of the upper segment half, preparatory to splitting; and FIG. 9 shows the prior art technique for rotating a remaining segment half preparatory to troughing it on the far side of the capsule.

FIGS. 10–17 illustrate nucleus rotating devices and a rotating method in accordance with the present invention. More particularly, FIG. 10 is perspective view of one form of rotator;

FIG. 11 is a plan view which shows the rotation of the segment halves using the rotator tool shown in FIG. 10;

FIG. 12 shows a second form of rotator which is a mirror image of the rotator device shown in FIG. 10;

FIG. 13 shows a remaining segment half being rotated with the rotator device of FIG. 12;

FIG. 14 is a diagrammatic cross section showing the face of the rotator engaging a segment;

FIG. 15 is a plan view of an alternative form of rotator, having a pivotable bar;

FIG. 16 is an enlarged axial section of the tool of FIG. 15, showing the bar rotating mechanism;

FIG. 17 is a diagrammatic plan view showing the bar inserted in a trough and being rotated to turn two segment halves prior to quartering;

FIGS. 18-26 illustrate nucleus splitting devices and a splitting method in accordance with the invention. More particularly, FIG. 18 is a plan view of one form of cracker, inserted in a troughed nucleus prior to splitting;

FIG. 19 is a cross-sectional view taken on line 19—19 of FIG. 18;

FIG. 20 is a view similar to FIG. 18 but shows the cracker opened and the nucleus split;

FIG. 21 is a cross-sectional view taken on line 21—21 of FIG. 20;

FIGS. 22 and 23 illustrate a second form of nuclear cracker, FIG. 22 being a longitudinal section showing the blades in the closed position, and FIG. 23 a diagrammatic view showing the blades in open position;

FIG. 24 is an enlarged perspective view of a preferred form of cracker combined with a phako tool, in which the cracker is incorporated in a sleeve through which fluid can be injected into the eye, showing the blades in closed position;

FIG. 25 is a view similar to FIG. 24 but shows the blades in open position; and

FIG. 26 is an axial section of the tool shown in FIG. 25.

DETAILED DESCRIPTION

Figure 1:
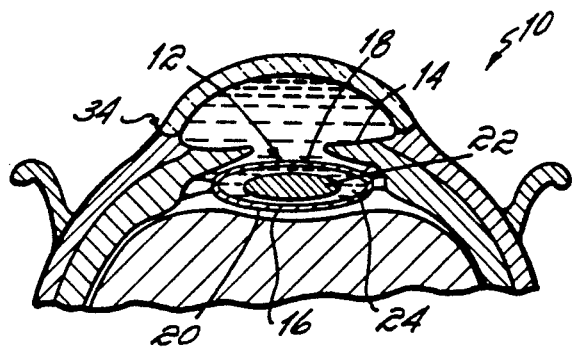
FIG. 1 is a diagrammatic cross section of the human eye.

As shown in FIG. 1, the human eye, designated generally by 10, has a lens 12 which is situated behind the iris 14. Lens 12 includes an outer covering or capsule 16, the frontal portion 18 of the capsule being known as the anterior capsule, and the rearward or inner portion 20 of the capsule being known as the posterior capsule. Inside the capsule the lens core or nucleus 22 is surrounded by a somewhat more fluid cortex 24. The devices of this invention are useful to separate and remove the nucleus 22 from the cortex and the capsule around it.

Figure 2:
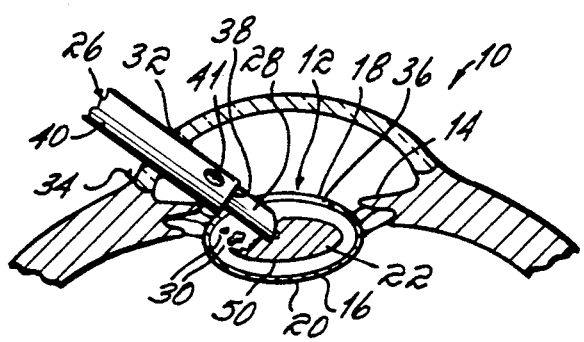
FIG. 2 is diagrammatic representation of the removal of a cataract nucleus by the conventional phakoemulsion technique.

In a first prior art phakoemulsification technique for removing a nucleus from its capsule 16, shown in FIG. 2, a primary incision 32 (as small as possible and usually about 3 mm wide) is made in the sclera-corneal junction 34 of the eye, and the anterior surface 18 of the capsule is cut away to provide an opening 36 into which the angulated tubular tip 28 of a phako tool 26 can be inserted. Tip 28 is vibrated axially at a high rate, e.g., 40,000 cps, at small amplitude, and erodes nucleus 22 into small fragments as indicated by 30. Flushing fluid, typically saline, is injected into the capsule through an annular space 38 between tip 28 and a sleeve 40 around the tip 28 and through side ports 41 in the sleeve. The nuclear fragments 30 are removed by aspiration through an axial opening 42 in tip 28.

Figure 3:
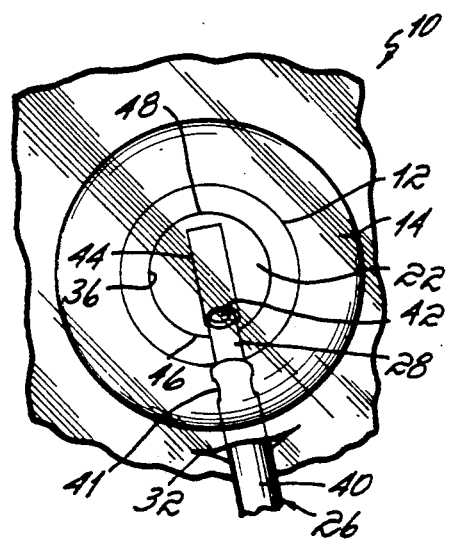
FIGS. 3 through 9 are a series of diagrammatic views showing sequential steps in the prior art fractional phako technique for removing a nucleus. More particularly.
Figure 4:
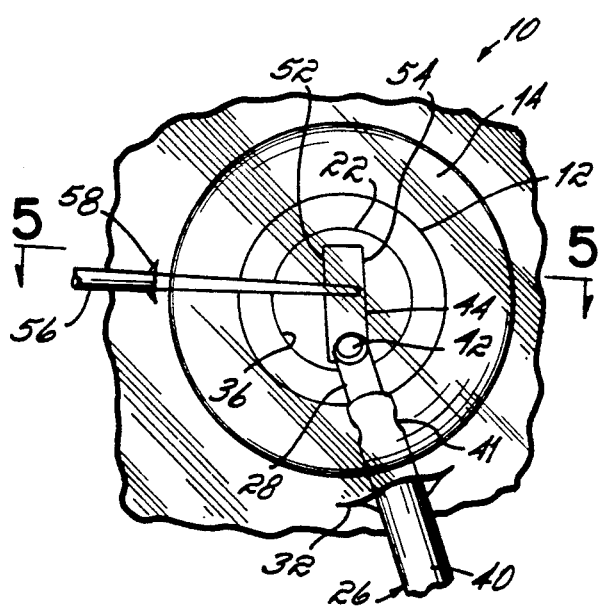
Figure 5:
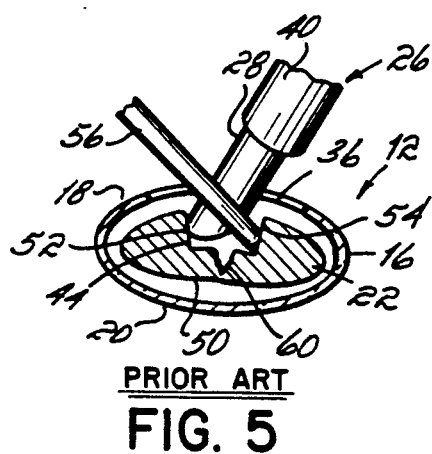
Figure 6:
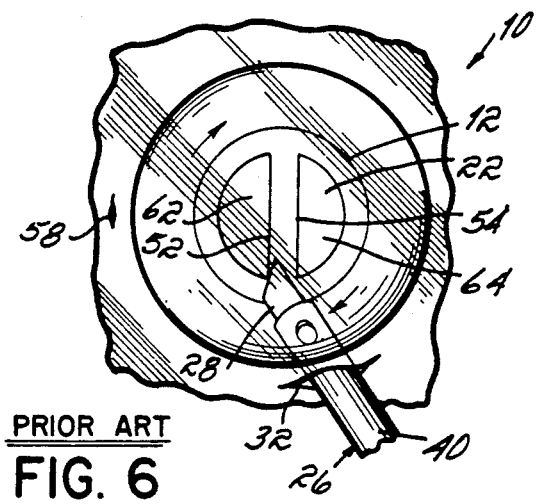
Figure 7:
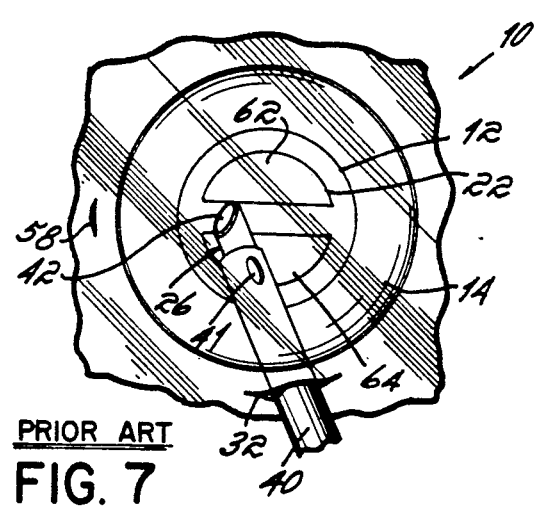
Figure 8:
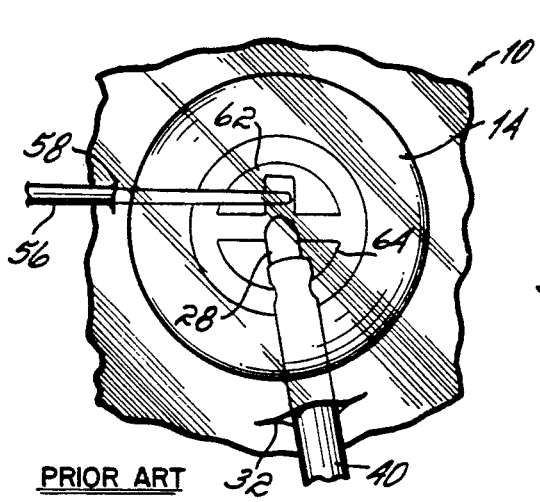
Figure 9:
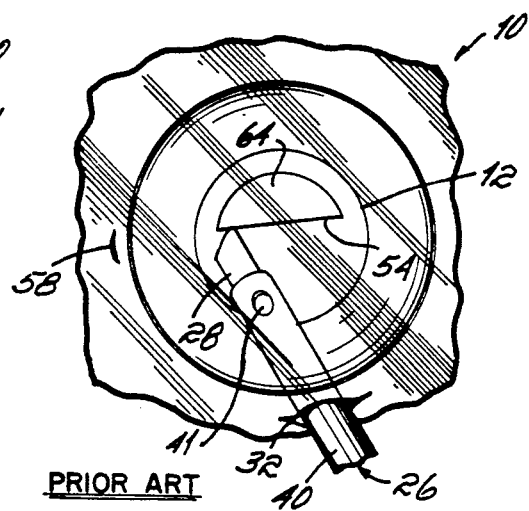

In the first phako technique shown in FIG. 2, essentially the entire nucleus 22 is fragmented; that is, it is not troughed or divided into smaller segments before emulsification. In the more recent fractional phako or "troughing" technique, a U-sectioned trough 44 is cut across the nucleus 22 with the phako tip. As shown in FIGS. 3-5, trough 44 does not extend either completely across nucleus 22 or completely through it; the trough stops short of both the near edge 46 and the far edge 48 of the nucleus, and does not extend to the posterior surface 50 of the nucleus (see FIG. 5). The sides 52, 54 of trough 44 are preferably flat and more or less straight. Trough is formed in a vertical direction, as viewed in FIG. 3, i.e., extending from the 12 o'clock position at the bottom of the eye to the 6 o'clock position at the top, it being easier to work the phako tip back and forth in that direction. (The phako tool is shown as positioned by a right-handed physician.) Once the nucleus 22 has been troughed, it is then split as shown in FIGS. 4 and 5. For this purpose a separate tool, a blunt probe 56, is inserted through a smaller (about 1 to 1.5 mm) secondary incision 58 at 9:00. The tip 28 of probe 56 extends across the trough and presses against its opposite wall 54; phako tip 28 presses against the other trough wall 52 so that the two tools are crossed, as shown in FIG. 5. The tip and probe press outwardly on the opposite walls of the trough to split the nucleus as at 60, within the capsule 16, which acts as a kind of bag during the procedure. The splitting step has heretofore been relatively difficult because two hands have been required to move the two tools in opposite directions sufficiently to split the nucleus, but not too hard for fear of damaging or rupturing the capsule. Moreover, a soft nucleus may not be cleaved readily or cleanly by the prior technique. Once split, the two nuclear segment halves 62, 64 (FIG. 6) are rotated 90° within the capsule ore either half is removed by phakoemulsification; the phakoemulsification is safer if the segment halves are split into segment quarters before they are emulsified. For this purpose the phako tip 28 is manipulated to nudge and turn the left half segment 62 inside the capsule (see FIG. 6). As that segment is moved, its upper end abuts the upper end of the right segment 64 and pushes that segment around, until the split between them is positioned horizontally across the capsule (FIG. 7). The segments are loosely attached to the cortex but they usually detach and become free while they are being rotated; the cortex should not be rotated. That done, the then upper half segment 62 is troughed, as shown in FIG. 8, and is split into two quarter segments, again using the probe 58 and the phako tip to press apart the opposite walls of the trough. The two segment quarters formed by splitting the upper segment half 62 are then phakoed and removed. The lower segment 64 is then the only segment remaining, and again for troughing it is pushed around to the top position, previously occupied by segment 62, and troughed. The phako tip is again used as the pusher (see FIG. 9). Unlike the first rotation (FIGS. 6 and 7) which was through 90°, this second rotation is through 180°. Half segment 64 is then troughed, split (again using the probe), and phakoed to remove it.

In accordance with this invention, the troughing and phakoemulsification steps themselves may proceed in accordance with the prior art techniques, but the rotating and/or splitting steps are different and are preferably carried out with use of special instruments in accordance with the invention.

Figure 10:
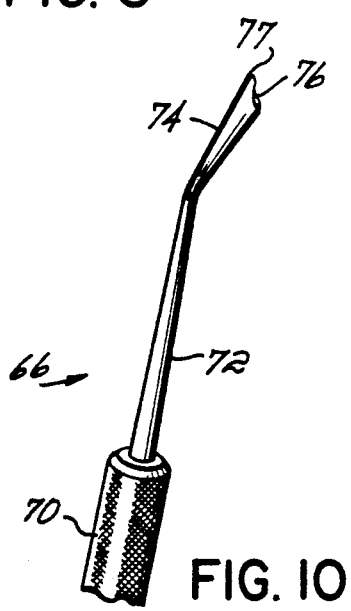
Figure 11:
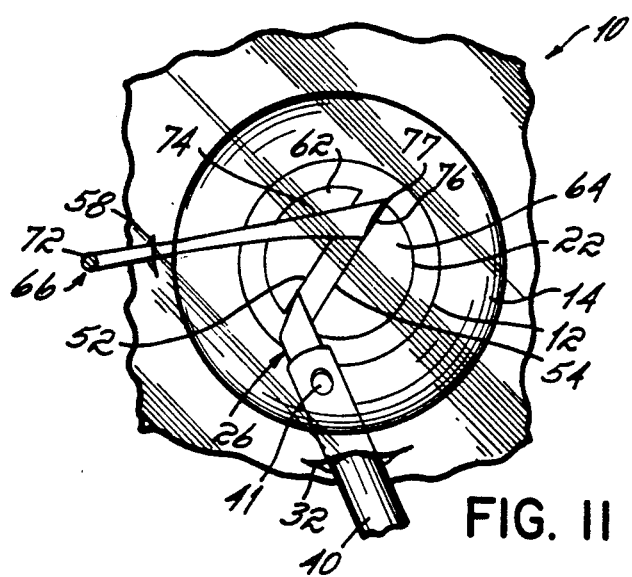

Presently preferred forms of rotator instruments and their use in accordance with the invention are shown in FIGS. 10-14. Preferably two different rotators, mirror images of one another as illustrated in FIGS. 10 and 12, are used. The first rotator 66, shown in FIG. 10, is used in the first rotating step to turn segment 64 clockwise 90°, after halving and prior to quartering it. The second rotator 68 (FIG. 12) is used to turn segment half 64 counterclockwise 180° after the first segment 62 has been quartered and removed (FIG. 13).

More specifically, each rotator 66, 68 has a hand gripper handle 70, a shank 72 having a diameter substantially less than the width of incision 58, and an angulated, enlarged or "elephant" foot 74 of larger transverse dimension than shank 72. The foot 74 of each rotator 66, 68 extends from its shank at an inside angle in the range of about 120° to 160° and preferably about 135°. Each foot has an end or face 76 which is preferably concave like a spoon, and which approximates the curvature of the surface of the nucleus which it is to engage. By reason of the angulation of the face 76 to the axis of the foot, the area of the face is larger than the cross-sectional area of the foot, and this relatively large area increases the pushing engagement of the foot with the segment. The secondary incision must be wide enough to permit the foot to be inserted through it but preferably no wider, and the pointed tip 77 of the foot facilitates the insertion. Once inserted, the shank (which is narrower than the foot) can be maneuvered in the incision. As can be seen by comparing FIGS. 10 and 12, when the first rotator 66 is oriented, its face 76 faces downwardly; whereas when the second rotator 68 is similarly oriented its face 76 faces upwardly. The manner in which the rotator face 76 engages the periphery of the nucleus 22 (shown in phantom) is shown in axial section in FIG. 14. Each rotator is inserted through secondary incision 58, but whereas the first rotator 66 engages the wall of the trough and turns the segment half clockwise through an angle of 90°, the second rotator 68 rotates the segment half in a counterclockwise direction, by 180°. Thus the angular relationship between the rotator face and the wall of the trough changes much more for the second rotator than the first. Maneuvering may be assisted by the pointed tip 77 at the outer end of the foot.

If a given nucleus is relatively soft and jelly-like, the rotators 66 and 68 may tend to pierce or spear it rather than to rotate it. I have therefore provided another form of rotator 78, shown in FIGS. 15, 16 and 17, which is especially useful in that situation. This rotator 78 has a handle and shank, at the outer end of which a tiny rotatable bar 80, receivable in the trough between the segment halves, is pivotally mounted (see FIGS. 15-17). The bar 80 lies beneath the tip of the shank of the device, and has a gear 82 extending upwardly into the hollow shank. Gear 82 is engaged by a drive or a worm gear 84 in the shank which may be turned by a shaft 86 at the other end of the handle (see FIG. 15). When shaft 86 is turned, worm gear 84 is rotated and slowly turns gear 82 from the insert position in which it is parallel to the shank of the device (FIG. 15), to a transverse position (FIG. 7). Bar 80 is shaped to be received within the trough between the segment halves. It can be seen that when rotated the bar 80 makes contact with the walls of the trough over a larger area than the faces of the rotators and thus provides a better "push," to rotate the segments 62, 64. (This rotator bar instrument is not usually used to rotate segment quarters.)

Several forms of cataract splitting devices in accordance with the invention are shown in FIGS. 18-26. In the simplest form, illustrated in FIGS. 18-21 a splitter 90 is provided which is separate from the phako tool 26. The splitter 90 has a handle 92 from the end of which extend a pair of stems having parallel opposed blades 94, 96 at their outer ends. The dimensions across the stems and across the blades in closed position are less than the width of the primary incision so that they can be inserted through it. Once inserted the blades (but not the shank) may open to a dimension greater than the incision width. Blades 94, 96 may be semicircular or spoon-shaped in section (see FIGS. 19 and 21), with their concave sides outward. Stems 98, 98 of the blades act as leaf springs and preferably but not necessarily tend to bias the blades apart from one another, to an open or cracking position (FIG. 20); the blades can be held together in the closed position (FIG. 18) by a blade operating sleeve 100 which is axially shiftable on the handle 92 of the splitter. When sleeve 100 is shifted axially away from the blades (downwardly as seen in FIG. 20), the springlike stems 98 of the blades urge them apart in the trough so that the blades 94, 96 engage the respective walls of the trough, pushing the walls apart and splitting the nucleus along the trough (FIG. 20). Only one tool is needed; moreover the blades, being relatively long in relation to the length of the trough, engage the wall over a relatively larger area than the probe and tool used in the prior art technique (FIG. 5), which helps to split a soft nucleus. The trough should be made no wider than the tip 28 of the phako tool requires, and in closed position the blades should just fit within it, without lateral play. If the dimension across the closed blades is too small, part of their opening movement is lost motion before the blades contact the walls (see FIG. 21). Initially the blades are used to split the nucleus into two segment halves, and are fitted in a relatively long trough (FIG. 18). Thereafter the blades are inserted in a trough which is only about half as long, to split the half segment into segment quarters Crackers having blades of different lengths appropriate for these two different splitting operations may be provided.

In the cracker 90 shown in FIG. 18, the blades are operated by shifting the sleeve 92 axially. FIGS. 22 and 23 show a related form of cracker in which blades 102, 104 are pivoted together so that one blade 102 is moved apart from the other blade 104 by pressing on a lever handle 106 at the end opposite from the blades. A spring 108 acts on lever handle 106 to bias the blades closed. This arrangement may be more convenient for the physician, since the blades can be operated more easily.

A different and preferred form of splitter 119 is shown in FIGS. 24-26. This splitter 119 comprises part of the phakoemulsifier tool itself and makes it unnecessary to remove the phakoemulsifier from the eye in order to use a separate splitter. In this embodiment the splitter 119 comprises two curved wings 110, 112 which form parts of a sleeve 116 around the tip 118 of the phako tool. The blades are integrally hinged to the sleeve by connection at their lower ends 114. The hinged wings 110, 112 are operated by control wires 120, 120 which are linked to push them open and pull them closed (see FIG. 26). When the wings are closed, saline or other fluid can be supplied to the lower end of this sleeve and delivered through it adjacent the tip 28, as in a conventional phako tip, to suspend the fragments during phakoemulsification. This form of cracker is especially useful since no second tool need be introduced for splitting.

Having described the invention, what is claimed is:

1. In the method of removing a cataract nucleus from a lens capsule wherein a trough is formed in the nucleus with a tool inserted through a first incision, the nucleus is split along the trough to form two smaller segments, the segments are rotated within the capsule and then removed by phako-emulsification, the improvement comprising, providing a splitting instrument having convexly rounded surfaces on opposite sides thereof adjacent an end of said instrument, said instrument being openable to move said surfaces outwardly away from one another, removing said tool from said first incision after said trough has been formed, and thereafter inserting said splitting instrument through said first incision and placing it within said trough between side walls thereof, and opening said splitting instrument so that said convexly rounded surfaces engage said side walls of said trough and apply force laterally to said side walls to push them apart and thereby split said nucleus into two segments along said trough.

2. The improvement of claim 1 further wherein said segments are rotated within said capsule by inserting a rotator instrument through a second incision spaced angularly from said first incision, and turning one of said segments with said rotator instrument while simultaneously turning the second said segment with a second instrument inserted through said first incision.

3. In the method of removing a cataract nucleus from a lens capsule wherein a trough is formed in the nucleus with a tool inserted through a first incision, the nucleus is split along the trough to form two smaller segments, the segments are rotated within the capsule and then removed by phyakoemulsification, the improvement comprising, rotating said segments within said capsule after said splitting by inserting a rotator instrument through a second incision spaced angularly from the first incision, and turning one of said segments with said rotator instrument while simultaneously turning the second of said segments with a second instrument inserted through said first incision, said first and second instruments being engaged with and pushing against opposite side walls of said trough after said nucleus has been split.

4. In the ophthalmological procedure of removing a cateract nucleus from a lens capsule wherein a trough is formed in the nucleus with a tool inserted through an incision, the nucleus is split along the trough to form two smaller segments, and said segments are removed, the improvement wherein said nucleus is split into said two segments with a single instrument, said improvement comprising, providing an instrument having convexly rounded surfaces on opposite sides thereof adjacent an end of said instrument, said instrument being openable to move said surfaces outwardly away from one another, inserting aid instrument through said incision and placing said outwardly rounded surfaces within said trough between side walls thereof, and opening said instrument to move said surfaces oppositely away from one another and against said side walls so as to press laterally on said walls and thereby split said nucleus along said trough into said two segments.

5. The improvement of claim 4 wherein said trough is formed by phakoemulsification.

6. The improvement of claim 5 wherein said instrument is inserted after said phakoemulsification.

7. The improvement of claim 4 wherein said surfaces are provided on adjacent blades of said instrument and said blades are moved apart from one another and perpendicularly into engagement with said side walls.

8. The improvement of claim 7 wherein said blades are engaged within said side walls substantially along the length of the side walls.

9. The improvement of claim 4 wherein said surfaces of said instrument engage said side walls of said trough when placed within said trough, prior to said opening of said instrument.

10. The improvement of claim 4 wherein said surfaces are spoon shaped and said walls of said trough are pushed apart by engaging said spoon-shaped blades of sad instrument against them.

* * * * *